United States Patent [19]
Bailey et al.

[11] Patent Number: 5,166,384
[45] Date of Patent: Nov. 24, 1992

[54] METHOD FOR THE REMOVAL OF SILOXANE DISSOLVED IN THE SOLVENT EMPLOYED IN THE PREPARATION OF TRIMETHOXYSILANE VIA METHANOL-SILICON METAL REACTION

[75] Inventors: Donald L. Bailey, Traverse City, Mich.; Thomas E. Childress, Newport, Ohio; Robert L. Ocheltree, Pennsboro, W. Va.; James S. Ritscher, Marietta, Ohio

[73] Assignee: Union Carbide Chemicals & Plastics Technology Corporation, Danbury, Conn.

[21] Appl. No.: 864,795

[22] Filed: Apr. 7, 1992

[51] Int. Cl.$^5$ .............................. C07F 7/18; C07F 7/04
[52] U.S. Cl. .................... 556/466; 556/450; 556/451; 556/457; 556/458; 556/470
[58] Field of Search ............... 556/466, 470, 450, 451, 556/457, 458

[56] References Cited

U.S. PATENT DOCUMENTS

| | | | |
|---|---|---|---|
| 3,072,700 | 7/1960 | de Witt | 260/448.8 |
| 3,775,457 | 9/1972 | Marsaka | 260/448.8 |
| 4,288,604 | 5/1980 | Magee | 556/470 |
| 4,727,173 | 3/1987 | Mendicino | 556/470 |
| 4,761,492 | 9/1987 | Childress et al. | 556/482 |
| 4,762,939 | 9/1987 | Mendicino | 556/470 |
| 4,999,446 | 6/1990 | Moody et al. | 556/470 |
| 5,084,590 | 1/1992 | Ritscher et al. | 556/470 |
| 5,103,034 | 4/1992 | Cho et al. | 556/470 |

OTHER PUBLICATIONS

Chemical Abstract (CA 102(4):26566p), 1985.
Chemical Abstract (CA68(22):96332n), 1968.
Chemical Abstract (CA115(2):10160j, 1991.
Chemical Abstract (CA82(16):99387j), 1975.
Chemical Abstract (CA113(26):233405c), 1990.
Chemical Abstract (CA85(8):47572h), 1976.
Chemical Abstract (CA104(8):52164s), 1986.
Chemical Abstract (CA87(6):40084h), 1977.
Chemical Abstract (CA86(12):74088g), 1977.
Chemical Abstract CA82(10):58900c, 1975.
Chemical Abstract CA73(22):110629b, 1970.
Chemical Abstract CA66(14):(14):56391h, 1967.
Chemical Abstract CA115(16):160864f, 1991.
Chemical Abstract CA73(10):46268d, 1970.
Chemical Abstract CA72(24):122393t, 1970.
Chemical Abstract CA66(22):95899z, 1967.
Chemical Abstract CA115(20):209987q, 1991.
Chemical Abstract CA105(26):228684y, 1986.
Chemical Abstract CA103(22):179485g, 1985.
Chemical Abstract CA93(22):205959m, 1980.
Chemical Abstract CA90(10):73076x, 1979.
Chemical Abstract CA83(2):11918v, 1975.
Chemical Abstract CA83(2):11808j, 1975.
Chemical Abstract CA78(8):44802c, 1973.
Chemical Abstract CA76(6):26207s, 1972.
Chemical Abstract CA82(14):87198k, 1975.
Chemical Abstract CA110(2):9794j, 1989.
Chemical Abstract CA102(4):26566p, 1985.
Chemical Abstract CA99(2):6980k, 1983.
Chemical Abstract CA92(16):130833j, 1980.
Chemical Abstract CA76(8):35060r, 1972.
Chemical Abstract CA99(20):159747q, 1983.
Chemical Abstract CA76(20):117411v, 1972.

*Primary Examiner*—Paul F. Shaver
*Attorney, Agent, or Firm*—B. L. Deppenbrock

[57] ABSTRACT

In a trimethoxysilane preparation from silicon metal and methanol which preparation uses a solvent, a method for removing a siloxane dissolved in the solvent, which method comprises contacting the solvent with a boron-oxygen compound, and optionally an alkali metal alkoxide such as sodium methoxide.

15 Claims, No Drawings

METHOD FOR THE REMOVAL OF SILOXANE DISSOLVED IN THE SOLVENT EMPLOYED IN THE PREPARATION OF TRIMETHOXYSILANE VIA METHANOL-SILICON METAL REACTION

FIELD OF THE INVENTION

The present invention relates to a process for converting silicon metal and methanol to trimethoxysilane (TMS), which process employs a solvent to disperse the silicon metal in a fluid state (slurry). More Particularly, the present invention relates to an improvement in the process of producing trimethoxysilane from silicon metal and methanol by providing a method for removing undesirable siloxanes which are dissolved in the solvent during the reaction process.

PRIOR ART

The reaction between silicon metal and alcohol to produce trimethoxysilane is well-established. The so-called "direct" reaction between silicon metal and an alcohol, such as methanol, to produce a trialkoxysilane, such as trimethoxysilane, has been described in U.S. Pat. Nos. 3,775,547; 4,727,173; 4,761,492;, 4,762,939; 4,999,446 and 5,084,590. In both the batch and continuous processes described in these patents, it is preferable to employ one or more liquid solvents to disperse the silicon metal in a slurry. There has been an on-going need to make the direct reaction process commercially attractive. It has now been discovered that as the reaction proceeds, one or more siloxanes can become dissolved in the solvent. The contamination of the solvent by the dissolved siloxane limits the recyclability and/or reusability of the solvent and results in the solvent being discarded.

Accordingly, a need exists for a method of removing the siloxane dissolved in the solvent employed in a direct reaction process in order for the process to be more commercially attractive. Removal of the siloxane dissolved in the solvent would make the solvent recyclable in the direct reaction process or reusable in a subsequent process, thereby, reducing the overall cost of the trimethoxysilane preparation.

SUMMARY OF THE INVENTION

The present invention provides a method for removing siloxane dissolved in the solvent used in trimethoxysilane preparation from silicon metal and methanol, which method comprises contacting the solvent having siloxane dissolved therein with a boron-oxygen compound.

DETAILED DESCRIPTION OF THE INVENTION

Processes for producing trimethoxysilane frequently utilize a solvent to disperse the silicon metal in a slurry. Solvents useful in such processes are inert, that is, a solvent that does not substantially and/or significantly degrade under the reaction conditions of the process. Generally the inert solvent employed in the process is a high temperature stable organic solvent. Suitable inert solvents that may be employed include paraffinic hydrocarbons (e.g., dodecane); polyalkylated aromatic hydrocarbons (e.g., THERMINOL® 59, THERMINOL® 60, THERMINOL® 66); and mixtures thereof. Polyalkylated aromatic hydrocarbons and mixtures thereof are preferred solvents in such processes. The most preferred solvent is THERMINOL® 59.

THERMINOL® is the Monsanto Company tradename for heat transfer fluids having thermal stability and low vapor Pressure, i.e., not higher than about 170 Torr at 250° C.

The amount of solvent employed in a process for preparing trimethoxysilane is a function of the amount of silicon metal employed in the process. Generally, from one part solvent per two parts silicon metal (1:2) to four parts solvent per one part silicon metal (4:1) will be required. Usually this ratio will range from 1:1 to 2:1.

Generally, after a process batch, the reactor is cooled and the spent slurry (i.e., liquid solvent containing solids such as silicon metal and catalyst particles) is removed. Usually spent slurry is discarded. Alternatively, the spent slurry is filtered by means well-known to those skilled in the art to separate the solvent from the solids. The filtered solvent may be recycled to the process or reused in a subsequent process batch. However, at some point in the process the recycled or reused solvent will cause a problem in the reactor, known as "reactor foaming" or "frothing". By reactor foaming or frothing is meant that the slurry effervesces such that the direct reaction process components (silicon metal, solvent and catalyst) can no longer be contained by the reaction vessel.

While not wishing to be bound by theory, the inventors have speculated that residual or by-product siloxanes of the process are dissolved in the solvent. It is thought that these residual or soluble siloxanes act as a surfactant and cause or contribute to the problem of reactor foaming or frothing. Infrared analysis, gravimetric analysis for silicon, and treating of the used solvent with caustic to generate hydrogen from the SiH specie support this theory and suggest that the siloxanes are a mixture of polydimethoxysiloxane, and smaller quantities of poly(hydridomethoxy)(dimethoxy) siloxanes and tetramethoxysilane (TTMS). Accordingly, it has been discovered that these dissolved siloxanes can be removed from the solvent by contacting the solvent with at least one boron-oxygen compound.

Any boron-oxygen compound that can effect the precipitation of the dissolved siloxane in the solvent can be employed in the method of this present invention. In the method of the present invention the solvent is contacted with a boron-oxygen compound selected from the group consisting of boric acid ($H_3BO_3$ or $B(OH)_3$), boric anhydride (also known as boric oxide, $B_2O_3$), sodium metaborate ($NaBO_2$), sodium orthoborate ($Na_3BO_3$), potassium metaborate ($KBO_2$), potassium orthoborate ($K_3BO_3$) and trimethylmetaborate (($CH_3O$-$BO$)$_3$) and mixtures thereof. Preferably, the boron-oxygen compound is selected from the group consisting of boric acid, boric anhydride, and sodium metaborate. Boric acid is the most preferred boron-oxygen compound since it is effective in removing the dissolved siloxane, readily commercially available and inexpensive. Lithium and cesium borates are generally not preferred since they are costly and not readily available. Magnesium and calcium borates are also not desirable since they do not produce a precipitate and, hence, are unreactive with the dissolved siloxane. While precipitation of the dissolved siloxane has been attempted using other metal-oxygen compounds, such as an aluminum-oxygen compound or a phosphorus-oxygen compound, these compounds have not been found to work in the present invention. Metal-oxygen compounds such as a tin-oxygen compound or a bismuth-oxygen compound can produce a precipitate which is considered to be hazardous for disposal and, therefore, these compounds are not desirably employed in the present invention.

Any amount of dissolved siloxane in the solvent can be removed by contacting the solvent with the boron-oxygen compound. However, the amount of boron-oxygen compound employed in the method of the present invention is a function of the percent siloxane (as Si) dissolved in the solvent. Generally, from 0.1 part boron-oxygen compound per 1 part siloxane (as Si) to 10 parts boron-oxygen compound per 1 part siloxane (as Si) in the solvent will be required. Preferably this ratio ranges from 0.5:1 to 2:1. The most preferred ratio is 1:1.

While not wishing to be bound by theory, it is believed that when the solvent containing dissolved siloxane is contacted with a boron-oxygen compound, the boron-oxygen compound effects crosslinking of the siloxane such that a crosslinked siloxane precipitates out of the mixture of the solvent and the boron-oxygen compound. In general, when the solvent has been filtered to remove solids such as silicon metal and Cu particles prior to the addition of the boron-oxygen compound, the precipitate which forms is a hard, granular solid having an off-white or grayish color. If the solvent is not filtered to remove solids prior to being treated with the boron-oxygen compound, the precipitate is still a hard, granular solid, but it has a tan-to-brownish black color. Additionally, when the solvent is not filtered to remove solids before it is contacted with the boron-oxygen compound, more of such compound is generally needed for precipitation of the siloxane dissolved in the solvent. However, commercially it is generally more desirable to perform a single filtration step; in which case, the solvent is not filtered to remove the solids prior to being contacted with the boron-oxygen compound.

While a granular precipitate will form on standing in the mixture of the boron-oxygen compound and solvent over time (up to several weeks), it is highly desirable to reduce the time required to effect separation. In the method of the present invention, the time required for siloxane removal can be effectively reduced by agitation using means well-known to those skilled in the art. Such means include, for example, but are not limited to, jet mixing, gas sparging and mechanical agitation. Of these, it is preferred to mechanically agitate the mixture of the solvent and boron-oxygen compound.

It has further been discovered that heating the mixture of the solvent and the boron-oxygen compound increases the rate at which precipitation occurs. When the mixture is heated the temperature ranges from about 60° C. to about 150° C., and is preferably about 80° C. to about 120° C. Experimental work has revealed that when boric acid is employed as the boron-oxygen compound, the precipitation is effected at 60° C. to 120° C. When boric anhydride is employed as the boron-oxygen compound, the precipitation is effected at 80° C. to 150° C. That is, at the same temperature, boric anhydride effects the reaction at a slightly slower rate than boric acid.

In the method of the present invention, in a preferred embodiment the rate of removal of siloxanes dissolved in the solvent can be increased by the addition of an alkali metal alkoxide selected from the group consisting of a sodium alkoxide, a potassium alkoxide and mixtures thereof. Of these alkali metal alkoxides, sodium methoxide (NaOCH$_3$) and potassium methoxide (KOCH$_3$) are preferred. Sodium methoxide (also known as sodium methylate) is most preferred.

Alkali metal alkoxides are readily commercially available. For example, sodium methoxide is commercially available from Occidental Chemical Company as a 25% solution in methanol or as a solid from Aldrich Chemical Company. Of the liquid sodium methoxide and solid sodium methoxide, it is preferred to use the solid form of sodium methoxide. Upon addition to the solvent, the liquid sodium methoxide produces a slight foaming phenomenon, while the solid sodium methoxide does not foam when added to the solvent. The sodium methoxide can be added simultaneously or sequentially with the boron-oxygen compound. Preferably the sodium methoxide is added simultaneously with or prior to the addition of the boron-oxygen compound. In a most preferred embodiment the sodium methoxide is added to the solvent containing dissolved siloxane about 1 minute to about an hour before the addition of the boron-oxygen compound, such as boric acid, with heating at a temperature ranging from about 80° C. to 120° C. for about one hour.

While not wishing to be bound by any particular theory, it is believed that the sodium methoxide opens or breaks the siloxane chain forming a sodium silanolate which in turn reacts or crosslinks with the boron-oxygen compound to yield a hard, granular precipitate. While other sodium or potassium alkoxides such as, for example, sodium ethoxide or potassium ethoxide, can be employed in the method of the present invention, they are not preferred because they can produce alcohols other than methanol used in trimethoxysilane preparation. Therefore, potentially the trimethoxysilane preparation reaction could become contaminated by these other alcohols, such as, for example, ethanol. Other alkali metal alkoxides such as lithium methoxide, for example, are not generally preferred since high temperature and/or pressure are required to effect crosslinking of the siloxane.

The amount of alkali metal alkoxide employed in the method of the present invention is based upon the amount of the boron-oxygen compound employed. Generally, the amount of the alkali metal alkoxide employed is a stoichiometric amount, or less than the stoichiometric amount, based on the amount of boron-oxygen compound employed. If more than the stoichiometric amount of alkali metal alkoxide, which acts as a base, were to be employed in treating the solvent, after treatment there would remain in the solvent an excess of the alkali metal alkoxide. Excess alkali metal alkoxide in the solvent is detrimental to the preparation of trimethoxysilane. For example, the stoichiometric amount of sodium methoxide employed based upon the amount of boric acids employed is calculated as follows:

$$\text{parts (NaOCH}_3\text{)} = 3 \times \frac{\text{MW(NaOCH}_3\text{)}}{\text{MW(H}_3\text{BO}_3\text{)}} \times \text{parts (H}_3\text{BO}_3\text{)}$$

$$= 3 \times \frac{54}{62} = \frac{162}{62} = 2.6$$

MW = molecular weight

Thus, a ratio of about 2.6 parts sodium methoxide to 1.0 parts boric acid could be used, because 162 parts by weight of pure sodium methoxide will exactly neutralize 62 parts by weight of boric acid. For sodium methoxide and boric anhydride the stoichiometric amount is calculated as follows:

$$\text{parts (NaOCH}_3\text{)} = 6 \times \frac{\text{MW(NaOCH}_3\text{)}}{\text{MW(B}_2\text{O}_3\text{)}} \times \text{parts (B}_2\text{O}_3\text{)}$$

$$= 6 \times \frac{54}{70} = \frac{324}{70} = 4.6$$

MW = molecular weight

Generally, a range of from 1:10 to 1:1 parts by weight of alkali metal alkoxide per 1 part boron-oxygen compound is used. Preferably, the amount of alkali metal alkoxide employed ranges from about 1:5 to 1:1. A ratio of one part alkali metal alkoxide to three parts boron-oxygen compound (1:3) is most preferred.

Any means known to those skilled in the art can be used to separate the siloxane precipitate from the "rejuvenated" solvent (i.e., the solvent from which dissolved siloxane has been removed). Such separation means may include, for example, settling, filtering, pressurized filtering and centrifuging. Preferred among these is pressurized filtering and basket centrifuging.

Once the siloxane precipitate has been removed from the solvent, the rejuvenated solvent may be introduced into the trimethoxysilane preparation reaction by means known to those skilled in the art. For example, the solvent can be introduced into the trimethoxysilane preparation reaction by pumping, pouring or pressurized transfer.

Whereas the exact scope of the instant invention is set forth in the appended claims, the following specific examples illustrate certain aspects of the present invention. However, the examples are set forth for illustration only and are not to be construed as limiting on the present invention. All parts and percentages are by weight unless otherwise specified.

MEASUREMENT OF % DISSOLVED SILOXANE (as Si) USING INFRARED ANALYSIS

In the examples, % siloxane (as Si) was obtained by infrared analysis according to the following procedure. A calibration curve for infrared analysis was developed using a gravimetric method for determining % siloxane (as Si). The calibration curve is a plotting of % siloxane (as Si) versus infrared absorbance.

Accordingly, aliquots of 3 or 4 samples are each analyzed gravimetrically as follows: A 1-gram aliquot is cooled in dry ice. To the aliquot is added 5-cc of fuming $H_2SO_4$. The dry ice is removed and the aliquot is heated to drive off $SO_3$ and then heated to dryness. The aliquot is further heated to 400° C. to drive off carbon as $CO_2$ and finally heated to 900° C. The aliquot is cooled to room temperature and weighed (W1). Two drops of $H_2SO_4$ and 5-cc of HF are added to the aliquot which is heated to dryness and then heated to 900° C. The aliquot is cooled to room temperature and weighed (W2). The grams of $SiO_2$ equals (W1) minus (W2).

Aliquots of the same 3 or 4 samples are measured by IR using the following procedure. A 1-cc aliquot of each sample is diluted with 10-cc of $CCl_4$. The absorbance of the sample is scanned from 1320 $cm^{-1}$ to 920 $cm^{-1}$. A peak at about 1100 $cm^{-1}$ corresponds to the dissolved silicon. By plotting the % Si versus the absorbance for each of the samples a calibration curve is developed.

The solvent employed in these examples was Therminol ® 59.

EXAMPLES 1-6

Effect of Boric Acid on Siloxane Removal

The solvent employed in Examples 1-6 had been used in a trimethoxysilane preparation via the methanol-silicon reaction similar to the preparation as described in U.S. Pat. No. 4,999,446. The solvent was filtered by means of a pressure filter with a 2.5-5.0 micron pad to remove solids such as silicon metal and catalyst. According to infrared analysis, the solvent contained 2.55% dissolved siloxane (as Si).

EXAMPLE 1

To a 250-ml three-neck flask equipped with a magnetic stirrer, thermometer, and a nitrogen purge vent were charged 25 grams of solvent. To the solvent were added 0.625 grams of boric acid (Fisher Scientific #A-73). The contents of the flask were stirred and heated to 80° C. using a Potwatcher ® for 2 hours. After 2 hours, the flask was cooled to below 50° C. The solvent was filtered to remove an off-white precipitate (crosslinked siloxane) using a 0.45 micron filter and about 35 pounds of $N_2$ pressure. Using infrared analysis the filtered solvent was analyzed for % siloxane (as Si) removal. The result is set forth in Table 1.

Examples 2-6 were prepared as in Example 1 except that the amounts of boric acid used were as set forth in Table 1. The % siloxane (as Si) removal for Examples 2-6 is set forth in Table 1.

It can be seen from Table 1 that the higher the loading of boric acid the greater the amount of dissolved siloxane removed from the solvent. For example, in Table 1, a boric acid to siloxane (as Si) ratio of 0.1 (Example 1), resulted in a 30% siloxane removal; a boric acid to siloxane (as Si) ratio of 2 (Example 6), resulted in 100% of the siloxane being removed.

TABLE 1

| Example # | Grams boric Acid Per 25 Grams Solvent | Grams boric Acid Per Gram Siloxane (as Si) | % Siloxane in Filtered Solvent | % Siloxane (as Si) Removed from Solvent |
|---|---|---|---|---|
| 1 | 0.0625 | 0.1 | 1.79 | 30 |
| 2 | 0.125 | 0.2 | 1.31 | 49 |
| 3 | 0.188 | 0.3 | 1.08 | 58 |
| 4 | 0.25 | 0.4 | 0.78 | 69 |
| 5 | 0.375 | 0.6 | 0.28 | 89 |
| 6 | 1.25 | 2.0 | 0 | 100 |

EXAMPLES 7-12

Effect of Temperature on Siloxane Removal

The procedure set forth in Example 1 was followed except that 0.25 grams of boric acid per 25 grams of solvent was used at the times and temperatures set forth in Table 2. According to infrared analysis, the solvent employed in Examples 7-12 contained 2.55% dissolved siloxane (as Si).

It can be seen from Table 2 that a longer residence time or contacting time results in more dissolved siloxane being removed from the solvent. For example, at 50° C. and a 1-hour residence time (Example 9), 13% of the dissolved siloxane is removed from the solvent; at 50° C. and a 4-hour residence time (Example 11), 55% of the siloxane is removed from the solvent. Also Table 2 illustrates that operating at higher temperature results in more siloxane being removed. For example, from Example 9 in Table 2, it can be seen that 1-hour residence time at 50° C. resulted in 13% siloxane removal; while 1-hour at 80° C. resulted in 53% siloxane removal.

TABLE 2

| Example # | Time, Hrs. | % Si in Filtered Solvent at 50° C. | % Si Removal from Solvent at 50° C. | % Si in Filtered Solvent at 80° C. | % Si Removal from Solvent at 80° C. |
|---|---|---|---|---|---|
| 7  | 0   | 2.54 | 0.4 | 2.47 | 3  |
| 8  | 0.5 | 2.47 | 3   | 1.35 | 47 |
| 9  | 1   | 2.21 | 13  | 1.21 | 53 |
| 10 | 2   | 1.37 | 46  | 1.00 | 61 |
| 11 | 4   | 1.14 | 55  | 0.93 | 64 |
| 12 | 6   | 1.14 | 55  | 0.92 | 64 |

EXAMPLES 13–18

Effect of Temperature on Siloxane Removal Using Boric Anhydride

The procedure set forth in Example 1 was followed, except that 0.8 gm boric anhydride (Fisher Scientific #A-76) per 80 grams of solvent was used at the times and temperature set forth in Table 3. According to infrared analysis, the solvent employed in Examples 13–18 contained 2.70% dissolved siloxane (as Si). From Table 3, it can be seen that boric anhydride is effective in the removal of dissolved siloxane from the solvent and that longer residence time and higher temperature results in increased siloxane removal.

TABLE 3

| Example # | Time | % Siloxane in Filtered Solvent at 80° C. | % Siloxane Removal from Solvent at 80° C. | % Siloxane in Filtered Solvent at 120° C. | % Siloxane Removal from Solvent at 120° C. | % Siloxane in Filtered Solvent at 160° C. | % Siloxane Removal from Solvent at 160° C. |
|---|---|---|---|---|---|---|---|
| 13 | 0   | 2.46 | 9  | 2.41 | 11 | 2.30 | 15 |
| 14 | 0.5 | 2.08 | 23 | 1.83 | 32 | 2.11 | 22 |
| 15 | 1   | 1.87 | 31 | 1.17 | 57 | 2.30 | 15 |
| 16 | 2   | 1.31 | 51 | 0.87 | 68 | 2.23 | 17 |
| 17 | 4   | 1.02 | 62 | 0.66 | 76 | 2.16 | 20 |
| 18 | 6   | 0.59 | 78 | 0.66 | 76 | 2.19 | 19 |

EXAMPLES 19 (CONTROL) AND 20

Effect of Using Solvent Treated with Boric Acid in Trimethoxysilane Preparation

EXAMPLE 19 (Control)

Trimethoxysilane preparation in Example 19 was conducted substantially in accordance with the preparation described in U.S. Pat. No. 4,999,446.

To a stainless steel reactor (6" diameter × 13" high) equipped with an agitator having a 6-blade flat turbine (2.5" diameter) were charged approximately 2140 grams solvent, 1070 grams silicon metal (50×200 mesh), 7.06 grams catalyst (Alfa ® Stabilized Cu-(OH)₂), and 0.5 cc defoamer (Union Carbide SAG ® 100). The contents of the reactor were agitated and heated to about 250° C. Methanol was fed continuously to the reactor. Gaseous reactor product was passed to an Oldershaw ® column (20 tray × 1" diameter). A lites stream containing TMS-MeOH azeotrope and unreacted methanol was removed from the column and returned to the reactor. Crude product containing TMS and small amounts of tetramethoxysilane (TTMS) was removed from the column in a heavies stream. The solvent was returned to the reactor twice (i.e., used in three batches or passes through the reactor). Before the solvent was passed to the reactor for a fourth batch, it was filtered by means of a pressure filter with a 2.5–5.0 micron filter pad to remove solids such as spent silicon metal and Cu particles. However, when the solvent was passed through the reactor for a fourth batch uncontrollable foaming occurred such that the reaction had to be discontinued. The results are set forth in Table 4.

EXAMPLE 20

The procedure set forth in Example 19 was followed, except that after the solvent containing dissolved siloxane from the third batch was filtered to remove spent silicon metal and catalyst particles, the solvent containing dissolved siloxanes was contacted with 0.74 parts of boric acid for every 1 part of dissolved siloxane (as Si) at 80° C. for 2 hours. The solvent was filtered by means of a pressure filter with a 2.5–5.0 micron filter pad to remove the precipitated siloxane. After this treatment, the solvent contained about 0.22% siloxane (as Si). The solvent was returned to the reactor for a fourth batch. The results are set forth in Table 4.

From Table 4, it can be seen that solvent recycled without treatment using a boron-oxygen compound (Example 19) to remove dissolved siloxane resulted in reactor foaming and difficulty in solvent filtration, and that treatment with a boron-oxygen compound (Example 20) reduced or eliminated foaming and improved solvent filtration. Since selectivity is an indicator of reactor performance, the selectivity results in Table 4 show that selectivity remained high (>10/1) after the solvent was treated with a boron-oxygen compound.

TABLE 4

| Example No. | Batch # | New Solvent/ New Makeup Solvent, gms* | % Siloxane in Solvent at Completion of Batch | Solvent Filtration Rate gm/hr-ft² | Average Selectivity (TMS over TTMS) | Cumulative Silicon Reacted, gms |
|---|---|---|---|---|---|---|
| 19 (Control) | 1 | 2140 | 0.85 | about 1600 | 13.0 | 1020 |
|  | 2 | 100 | 1.1 | about 250 | 12.9 | 1950 |
|  | 3 | 80 | 1.2 | about 300 | 13.9 | 2970 |
|  | 4 | Reaction foamed | — | — | — | — |
| 20 | 1 | 2140 | 0.95 | about 1700 | 13.4 | 1015 |
|  | 2 | 100 | 1.14 | about 300 | 10.7 | 1989 |
|  | 3 | 55 | 1.35 | about 300 | 15.7 | 2976 |

TABLE 4-continued

| Example No. | Batch # | New Solvent/ New Makeup Solvent, gms* | % Siloxane in Solvent at Completion of Batch | Solvent Filtration Rate gm/hr-ft$^2$ | Average Selectivity (TMS over TTMS) | Cumulative Silicon Reacted, gms |
| --- | --- | --- | --- | --- | --- | --- |
| | 4 | 330 | 0.91 | about 1700 | 21.9 | 3947 |

*Recycled solvent plus new makeup solvent equaled approximately 2140 grams for each of the batches.

EXAMPLE 21

Effect of Contacting Solvent With Sodium Methoxide

At the end of a batch for trimethoxysilane preparation in a 1.5-liter Chemineer ® reactor, 2345 grams of solvent having 1.06% dissolved siloxane (as Si) and spent solids (silicon metal and copper catalyst particles) were treated as follows. With agitation the reactor contents (solvent and solids) were heated to about 65° C. Sodium methoxide powder (10.07 grams, approximately 0.5 wt %) was added as the solid to the reactor contents. After about 1 minute, 30 grams (1.5 wt %) boric acid powder was added to the reactor contents. The reactor contents were heated to about 85° C. for 1 hour while agitation continued. The contents of the reactor were cooled to 40° C. and were filtered using a laboratory pressure filter fitted with a 2.5 to 5 micron filter pad. Pressure was maintained at 35 pounds nitrogen. After filtering, 1900 grams of solvent containing 0.25% dissolved siloxane (as Si) were recovered. Example 21 illustrates that dissolved siloxane can be removed from the solvent without first removing the solids produced by the trimethoxysilane preparation.

EXAMPLE 22

Effect of Filtering Solvent to Remove Solids

Spent slurry (1830 grams) containing about 1655 grams of solvent having 0.32% dissolved siloxane (as Si) and 175 grams of solids (silicon in Cu particles) was contacted with 10.7 grams (0.64 wt %) boric acid. The mixture of the slurry and boric acid was agitated and heated to 80° C. for 2 hours. The mixture was then cooled to about 40° C., filtered by means of a pressure filter with a 2.5-5.0 micron filter pad and analyzed for siloxane (as Si). Analysis revealed that the solvent contained about 0.22% siloxane (as Si). That is, the boric acid treatment had removed about 30% of the dissolved siloxane in the solvent. Next, the filtered solvent containing 0.22% siloxane (as Si) was treated with 0.5 wt % boric acid with agitation at 80° C. for 30 minutes. After cooling and filtration the level of dissolved siloxane in the solvent was undetectable. This example illustrates that filtering to remove solids before treating with boric acid is effective in the removal of dissolved siloxane from the solvent.

EXAMPLES 23 AND 24

Effect of Sodium Methoxide

EXAMPLE 23

One hundred grams of spent solvent containing dissolved siloxane (estimated as containing about 1.2% dissolved siloxane as Si) obtained from several trimethoxysilane preparations similar to those described in Example 22 was treated with 1.5 grams of boric acid for 1 hour at 80° C. with agitation. After the mixture of solvent and boric acid was cooled to below 40° C., the mixture was filtered through a pressure filter equipped with a 2.55 micron filter pad while maintaining 35 pounds nitrogen pressure on the filter. The filtration time for the mixture was 6 minutes. After this treatment, the rejuvenated solvent contained 0.34% dissolved siloxane.

EXAMPLE 24

The procedure set forth in Example 23 was repeated, except that 0.5 grams of D-16692 sodium methoxide was added to the solvent about 1 minute prior to the addition of the boric acid. The filtration time was 2.75 minutes. After this treatment the rejuvenated solvent contained 0.34% dissolved siloxane.

From Examples 23 and 24 it can be seen that amount of time required to filter is reduced by the addition of sodium methoxide.

EXAMPLE 25

In accordance with the procedure set forth in Example 1, solvent containing 4.4% dissolved siloxane (as Si) is treated using 1 part boric acid per 1 part dissolved siloxane (as Si), thereby removing the dissolved siloxane from the solvent. This example illustrates that the method of the present invention can be employed to remove higher levels of dissolved siloxane (as Si) from solvent used in trimethoxysilane preparation.

EXAMPLE 26

Pilot Scale Unit with Boric Acid Treatment of the Solvent

The procedure for the preparation of trimethoxysilane in this example was carried out in accordance with that described in Example 19 but on a larger scale and in accordance with the preparation described in U.S. Pat. No. 4,999,446. In all, five batches were carried out. Each batch used about 300 pounds of solvent and 0.66 pounds of a Cu(OH)$_2$ catalyst. Batch #1 used new, unused solvent. In Batches #2-5, solvent from the previous run and new make-up solvent was employed to maintain the 300 pound level of solvent in the reactor. After each batch (1-5), the spent slurry (solvent and solids) was filtered with a basket centrifuge equipped with a 5 micron filter bag. After Batches #3 and 4 the centrifuged slurry was filtered using a Sparkler ® filter. Slurry from Batch #4 was treated with 1 part (1 wt %) boric acid per 1 part dissolved siloxane at 80° C. for 2 hours. The boric acid treated slurry from Batch #4 was then centrifuged and filtered as above to remove precipitated siloxane. The results are set forth in Table 5. As the slurry from Batch #4 entered the reactor for Batch #5, it contained no detectable dissolved siloxane. The results also show that selectivity remained acceptable after treatment of the solvent with boric acid.

TABLE 5

| Batch # | Recycled Therminol 59 (lbs) | New Makeup* Therminol 59 (lbs) | Accumulated Silicon Reacted, (lbs) | % Dissolved Si at end of Batch | Reactor Foaming | Average Selectivity (TMS over TTMS) |
| --- | --- | --- | --- | --- | --- | --- |
| 1 | None | 300 | 41 | 1.1 | No | 2.2 |
| 2 | From Batch #1 | 30 | 82 | Not Measured | Yes, at start of batch only | 3.6 |
| 3 | From Batch #2 | 5 | 170 | 1.1 | Yes, throughout batch | 7.3 |
| 4 | From Batch #3 | 36 | 259 | 1.2 | Yes, throughout batch | 5.3 |
| 5 | From Batch #4 after Boric Acid Treatment | 31 | 347 | 0.43 | No | 6.0 |

*Recycled Therminol ® plus New Makeup Therminol ® equaled approximately 300 pounds for each batch.

We claim:

1. In a trimethoxysilane preparation from silicon metal and methanol which preparation uses a solvent, a method for removing a siloxane dissolved in the solvent, which method comprises contacting the solvent with a boron-oxygen compound.

2. A method according to claim 1 wherein the solvent is an inert solvent selected from the group consisting of paraffinic hydrocarbon, polyalkylated aromatic hydrocarbon and mixtures thereof.

3. A method according to claim 2 wherein the solvent is a polyalkylated aromatic hydrocarbon.

4. A method according to claim 1 wherein the solvent is filtered to remove silicon metal and copper particles prior to contacting the boron-oxygen compound.

5. A method according to claim 1 wherein the boron-oxygen compound is selected from the group consisting of boric acid, boric anhydride, sodium metaborate, sodium orthoborate, potassium metaborate, potassium orthoborate, trimethylborate and mixtures thereof.

6. A method according to claim 5 wherein the boron-oxygen compound is selected from the group consisting of boric acid, boric anhydride and mixtures thereof.

7. A method according to claim 1 wherein during the contacting step, the solvent is agitated and heated to about 60° C. to about 150° C.

8. A method according to claim 1 wherein the ratio of the boron-oxygen compound to % siloxane (as Si) dissolved in the solvent ranges from about 0.1:1 to about 10:1.

9. A method according to claim 1 wherein the solvent is additionally contacted with an alkali-metal alkoxide.

10. A method according to claim 9 wherein the alkali metal alkoxide is selected from the group consisting of sodium alkoxide, potassium alkoxide, and mixtures thereof.

11. A method according to claim 10 wherein the alkali metal alkoxide is selected from the group consisting of sodium methoxide and potassium methoxide.

12. A method according to claim 9 wherein the ratio of alkali metal alkoxide to boron-oxygen compound ranges from about 1:10 to about 1:1.

13. A method according to claim 9 wherein the alkali metal alkoxide is added to the solvent prior to contacting the solvent with the boron-oxygen compound.

14. A method according to claim 7, wherein the solvent is a polyalkylated aromatic hydrocarbon; the boron-oxygen compound is boric acid; the ratio of the boron-oxygen compound to % siloxane dissolved in the solvent is 1:1; and wherein the solvent is additionally contacted with sodium methoxide prior to contacting with the boron-oxygen compound.

15. A method according to claim 14 wherein the sodium methoxide to boron-oxygen compound ranges from about 1:5 to about 1:1.

* * * * *